United States Patent
Kumari et al.

(10) Patent No.: US 9,937,179 B2
(45) Date of Patent: Apr. 10, 2018

(54) COMBINED TREATMENT FOR CANCER RESISTANT TO AN EPIDERMAL GROWTH FACTOR RECEPTOR KINASE INHIBITOR

(71) Applicant: Pre Clinical Oncology Services Ltd., Belton (GB)

(72) Inventors: Rajendra Kumari, West Bridgford (GB); Andrew McKenzie, Arnold (GB)

(73) Assignee: CROWN BIOSCIENCE UK LTD, Belton (GB)

(*) Notice: Subject to any disclaimer, the term of this patent is extended or adjusted under 35 U.S.C. 154(b) by 0 days.

(21) Appl. No.: 14/679,897

(22) Filed: Apr. 6, 2015

(65) Prior Publication Data

US 2015/0283138 A1    Oct. 8, 2015

Related U.S. Application Data

(60) Provisional application No. 61/975,710, filed on Apr. 4, 2014.

(51) Int. Cl.
| | |
|---|---|
| *C12Q 1/68* | (2006.01) |
| *A61K 31/517* | (2006.01) |
| *A61K 31/4545* | (2006.01) |
| *A61K 45/06* | (2006.01) |
| *A61K 31/5377* | (2006.01) |
| *A61N 5/10* | (2006.01) |

(52) U.S. Cl.
CPC ........ *A61K 31/517* (2013.01); *A61K 31/4545* (2013.01); *A61K 31/5377* (2013.01); *A61K 45/06* (2013.01); *A61N 2005/1098* (2013.01)

(58) Field of Classification Search
None
See application file for complete search history.

(56) References Cited

U.S. PATENT DOCUMENTS

2006/0084666 A1   4/2006  Harari et al.
2012/0076777 A1   3/2012  McLeay

OTHER PUBLICATIONS

Huang et al (Cancer Res, 2013, 73(2): 824-833).*
Brand et al (Cancer Biology & Therapy, 2011, 12(5): 436-446).*
Chinnaiyan et al (Cancer Res, 2005, 65(8): 3328-3335).*
Yu et al (J Thorac Oncol, 2013, 8(3): 346-351).*
Yang et al (Int. J. Cancer, 2012, 132: E74-E84).*
Casado et al (Journal of Clinical Oncology, 2012, 30(15): 5520 Abstract).*
Xu et al (Clin Cancer Res, 2011, 17(13): 4425-4438).*
Calvo et al (Annals of Oncology, 2007, 18: 761-767).*

* cited by examiner

*Primary Examiner* — Sean E Aeder
(74) *Attorney, Agent, or Firm* — Jun He Law Offices P.C.; James J. Zhu (57) ABSTRACT

The present invention provides a method for treating a cancer, comprising (a) identifying a patient with acquired resistance to an EGFR kinase inhibitor; and (b) administering to the patient an anti-cancer agent, and treating the patient with radiation therapy.

12 Claims, 4 Drawing Sheets

COMBINED TREATMENT FOR CANCER RESISTANT TO AN EPIDERMAL GROWTH FACTOR RECEPTOR KINASE INHIBITOR

CROSS-REFERENCE TO RELATED APPLICATION

This application claims priority to U.S. provisional patent application No. 61/975,710, filed Apr. 4, 2014, titled "combined treatment for cancer resistant to an epidermal growth factor receptor kinase inhibitor", the disclosure of which is incorporated herein by reference in its entirety.

FIELD OF THE INVENTION

The present invention generally relates to treatment for cancer of acquired resistance to an EGFR kinase inhibitor.

BACKGROUND OF THE INVENTION

Cancer is a broad group of diseases involving unregulated cell growth. In cancers, cells divide and grow uncontrollably, forming malignant tumors, which may invade nearby parts of the body. Cancer cells may also spread to distant parts of the body through the lymphatic system or bloodstream. There are over 200 different known cancers that affect humans.

Over-expression of epidermal growth factor receptor (EGFR) kinase is often associated with many cancers, including breast, lung, colorectal and head and neck cancers, and is believed to contribute to the malignant growth of these tumors. Activation of EGFR stimulated signaling pathways promote multiple processes that are potentially cancer-promoting, e.g., proliferation, angiogenesis, cell motility and invasion, decreased apoptosis and induction of drug resistance. Accordingly, intense efforts have been made to develop anti-tumor agents that target EGFR kinase, e.g., compounds that directly inhibit the kinase activity of the EGFR, as well as antibodies that reduce EGFR kinase activity by blocking EGFR activation. And some EGFR kinase inhibitors have been shown to improve tumor cell or neoplasia killing when used in combination with certain other anti-cancer or chemotherapeutic agents or treatment.

Although many anti-cancer agents are typically quite effective as initial therapy, it is common for patients to develop resistance with long-term exposure to these anti-cancer agents. Often, despite more aggressive second and third course of therapy using these agents, cancer of acquired resistance to anti-cancer agents displays increasing resistance and eventually becomes virtual invulnerable to these agents. Therefore, there is a continuing need to develop therapy for cancer with acquired resistance to anti-cancer agents.

BRIEF SUMMARY OF THE INVENTION

The present invention provides a method for treating a cancer, comprising (a) identifying a patient with acquired resistance to a first EGFR kinase inhibitor; and (b) administering to the patient an anti-cancer agent, and treating the patient with radiation therapy.

In certain embodiments, the patient with acquired resistance to the first EGFR kinase inhibitor comprises a mutation of c-met gene. In some embodiments, the mutation of c-MET gene is an amplification of c-MET gene.

In some embodiments, the first EGFR kinase inhibitor is Erlotinib. In certain embodiments, the first EGFR kinase inhibitor is Gefitinib.

In some embodiments, the anti-cancer agent is a second EGFR kinase inhibitor. In certain embodiments, the second EGFR kinase inhibitor is the same as the first EGFR kinase inhibitor. In certain embodiments, the second EGFR kinase inhibitor is different from the first EGFR kinase inhibitor. In some embodiments, the second EGFR kinase inhibitor is Erlotinib.

In certain embodiments, the anti-cancer agent is not an EGFR kinase inhibitor. In certain embodiments, the anti-cancer agent is a c-Met inhibitor. In certain embodiments, the c-Met inhibitor is Crizotinib.

In certain embodiments, the cancer is a lung cancer. In certain embodiments, the cancer is NSCLC. In certain embodiments, the cancer is head and neck cancer.

In some embodiments, the drug is administered to the patient by parenteral or oral administration.

In certain embodiments, the method further comprises administering one or more other anti-cancer agents.

BRIEF DESCRIPTION OF FIGURES

FIG. 2A. Erlotinib resistant variant of NSCLC cell line (HCC827-ER1) harbors amplified c-MET gene copy number. Treatment naive and post-treatment resistance was characterized for mutations in EGFR by direct sequencing of exons 19 (del E746-A750) and 20 (T790M; gatekeeper). Exon 19 deletion was confirmed in all samples and no exon 20 T790M gatekeeper mutations were detected in any of the test samples. Samples were characterized for c-MET genomic amplification by qPCR.

FIG. 4B. The effect of Erlotinib and Crizotinib alone and in combination with irradiation in HCC827-ER1 subcutaneous xenograft. Tumor volume is expressed as a percentage of the initial dose volume, and error bars represent SEM. When nude mice bearing s.c. HCC827-ER1 tumors (n=5/ group) were dosed with Erlotinib or treated with irradiation, there was a significant reduction in tumor growth compared with vehicle (Two-way ANOVA, p<0.001; ~70% tumor growth inhibition) but no tumor regression. In clinical terms, this denotes progressive disease versus tumor regression and indicates treatment escape or emergence of resistance. When HCC827-ER1 tumors were dosed with Crizotinib there was a significant reduction in tumor growth compared with control (p<0.001; ~60% tumor growth inhibition), which confirmed the role of c-MET amplification in the resistance mechanism for HCC827-ER1. When Erlotinib or Crizotinib was combined with irradiation the tumor regression was restored, demonstrating benefit of combination of Erlotinib or Crizotinib with irradiation in Erlotinib resistant setting where there is a c-MET gene amplification.

DETAILED DESCRIPTION OF THE INVENTION

In one aspect, the present invention provides a method for treating a cancer, comprising (a) identifying a patient with acquired resistance to an EGFR kinase inhibitor; and (b) administering to the patient an anti-cancer agent, and treating the patient with radiation therapy.

The term "cancer" as used herein refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

The cancer maybe, for example, lung cancer, non small cell lung cancer (NSCLC), bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelia] dysplasia, adenomatous dysplasia, hereditary nonpolyposis colon cancer syndrome (HNPCC), Barrett's esophagus, bladder dysplasia, and precancerous cervical conditions. In certain embodiments, the cancer is NSCLC. In certain embodiments, the cancer is head and neck cancer.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

As used herein, the term "patient" refers to a human suffered from a cancer. In some embodiments, the term refers to a human in need of treatment for cancer with an EGFR kinase inhibitor. In some embodiments, the term refers to a human having being treated with an EGFR kinase inhibitor and demonstrates resistance to the EGFR kinase inhibitor. However, the term "patient" can also refer to non-human animals, preferably mammals such as dogs, cats, horses, cows, pigs, sheep and non-human primates, among others, that are in need of treatment with an EGFR kinase inhibitor.

"A patient of acquired resistance" refers to a patient when initially treated with an anti-cancer therapy, often an anti-cancer drug, demonstrate a beneficial therapeutic effect, but later becomes unresponsive to the therapy due to the repetitive administration thereof. In many cases, such resistance is caused by the appearance of cancer cells having acquired resistance to the anti-cancer drug. Drug resistance is often caused by alteration in the genes of cancer cells, when such gene products decrease transportation of drugs into cells or promote discharge of drugs out of cells, promote inactivation or detoxication of drugs, suppress conversion of a prodrug to an active-type drug, induce a decrease in a protein amount, to which a drug is targeted, or a decrease in the activity thereof, increase DNA repair activity, and suppress induction of apoptosis.

Acquired resistance to an anti-cancer therapy can be identified by the observation of unresponsiveness of the cancer to the therapy. This can be done by any method known in the art, including blood test, X-ray, CT scans, endoscopy, and conventional cancer pathology. In addition, cancer cells having acquired drug resistance to anti-cancer drugs can be identified by detecting the alternation of genes that have been found to be associated with acquired drug resistance (see US 20090143236 A1). The alternation of genes that have been associated with acquired drug resistance can be detected by any method known to a person skilled in the art. These methods include without limitation, PCR, quantitative-PCR, northern-blot, southern-blot, western-blot, gene sequencing.

In certain embodiments, the patient with acquired resistance to a first EGFR kinase inhibitor comprises a mutation of c-met gene. In some embodiments, the mutation of c-MET gene is an amplification of c-MET gene.

c-MET gene is a proto-oncogene that encodes a protein known as hepatocyte growth factor receptor (HGFR). c-Met is composed of the $\alpha$ chain and $\beta$ chain generated by cleaving a precursor of c-MET (pro c-Met) and forms a dimer by a disulfide linkage. c-Met is a receptor penetrating a cell membrane and the entire $\alpha$ chain and a part of the $\beta$ chain are present extracellularly (see, e.g., Mark, et al., The Journal of Biological Chemistry, 1992, Vol. 267, No. 36, pp. 26166-26171; Journal of Clinical and Experimental Medicine (IGAKU NO AYUMI), 2008, Vol. 224, No. 1, pp. 51-55). See also GenBank Accession No: NP_000236.2 for human c-Met and its $\alpha$ chain and $\beta$ chain. It has been shown that abnormal MET activation in cancer correlates with poor prognosis, where aberrantly active MET triggers tumor growth, formation of new blood vessels that supply the tumor with nutrients, and cancer spread or other organs.

EGFR Kinase Inhibitor

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase inhibitors include, for example, quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors (International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625).

Specific preferred examples of low molecular weight EGFR kinase inhibitors that can be used according to the present invention include [6,7-bis(2-methoxyethoxy)-4-quinazolin-4-yl]-(3-ethynylphenyl) amine (also known as OSI-774, erlotinib, or Tarceva™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); 3-[(1R)-1-(2,6-dichloro-3-fluoro-phenyl)-ethoxy]-5-(1-piperidin-4-yl/1-pyrazol-4-yl)-pyridin-2-amine (also known as crizotinib); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or Iressa™; Astrazeneca) (Woodburn et al., 1997, Proc. Am. Assoc. Cancer Res. 38:633).

In some embodiments, a low molecular weight EGFR kinase inhibitor that can be used according to the present invention is Erlotinib. Erlotinib (trade name Tarceva) is a drug of chemical name N-(3-ethynylphenyl)-6,7-bis(2-methoxyethoxy) quinazolin-4-amine, and has the following structure:

Erlotinib has been used to treat several types of cancer including non-small cell lung cancer (NSCLC) and pancreatic cancer.

In some embodiments, a low molecular weight EGFR kinase inhibitor is Grefitinib (trade name Iressa). Grefitinib has chemical name N-(3-chloro-4-fluoro-phenyl)-7-methoxy-6-(3-morpholin-4-ylpropoxy)quinazolin-4-amine and the following structure:

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or Erbitux™; Imclone Systems), ABX-EGF (Abgenix), EMD 72000 (Merck KgaA, Darmstadt), RH3 (York Medical Bioscience Inc.), and MDX447 (Medarex/Merck KgaA).

Additional antibody-based EGFR kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR kinase inhibitors useful in practicing the present invention also include anti-EGFR antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Anti-Cancer Agent

The term "anti-cancer agent" refers to any substance, compound or composition, when administered to a subject, has effect to inhibit, prevent or suppress cancer cell growth, proliferation or metastasis. Examples of the specific anti-cancer agent may include a c-MET inhibitor, an EGFR inhibitor, an ALK inhibitor, a PDGFR inhibitor, and a c-KIT inhibitor. Examples of the c-MET inhibitor may include PHA-665752, SU11274, XL-880, XL-184, ARQ 197, AMG208, AMG458, CE-355621, and MP470. Example of the EGFR inhibitor may include gefitinib, erlotinib, cetuximab, lapatinib, ZD6474, CL-387785, HKI-272, XL647, PD153035, CI-1033, AEE788, BIBW-2992, EKB-569, and PF-299804. Examples of the ALK inhibitor may include WHI-P154, TAE684, and PF-2341066. Examples of the PDGFR inhibitor may include Gleevec, Desatinib, Valatinib, and Pazopanib. Examples of the c-KIT inhibitor may include Imatinib, Sunitinib, Valatinib, Desatinib, Masitinib, Motesanib, and Pazopanib.

In some embodiments, the anti-cancer agent is an EGFR kinase inhibitor. In some embodiments, the EGFR kinase inhibitor is Erlotinib.

In some embodiments, the anti-cancer agent is a c-Met inhibitor. The term "c-Met inhibitor" is defined herein to refer to an agent that targets, decreases, or inhibitor activity of the c-Met receptor tyrosine kinase. Suitable c-Met inhibitor include ARQ197 (taventinib, developed by Daichi Sankyo and ArQule), AMG458 (developed by Amgen), GSK1363089 (also known as XL880 or foretinib, developed GSK), crizotinib (also known as PF2341066, developed by Pfizer), PF04217903 (developed by Pfizer), INCB28060 (developed by Incyte), E7050 (developed by Eisai), MK-2461 (developed by Merck), BMS-777607 (developed by BMS), JNJ-38877605 (developed by Johnson & Johnson), XL184 (developed by BMS/Exelixis).

In certain embodiments, the c-Met inhibitor is crizotinib. Crizotinib has chemical name 3-[(1R)-1-(2,6-dichloro-3-fluorophenyl)ethoxy]-5-(1-piperidin-4-ylpyrazol-4-yl)pyridin-2-amine and structure of:

The c-Met inhibitor also includes antibodies or fragments thereof that specifically binds to the c-Met protein and inhibits its activation. The c-Met inhibitor also includes small inhibitory RNA (siRNA) that functions to inhibit the expression of c-MET gene.

The anti-cancer agent will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the anti-cancer agent can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of anti-cancer agent being used (e.g., small molecule, antibody, RNAi or antisense construct), and the medical judgement of the prescribing physician as based, e.g., on the results of published clinical studies.

The amount of anti-cancer agent administered and the timing of anti-cancer agent administration will depend on the type (species, gender, age, weight, etc.) and condition of the patient being treated, the severity of the disease or condition being treated, and on the route of administration. Typically, the anti-cancer agent will be administered to the patient in a therapeutically effect amount. The term "therapeutically effective amount" or "effective amount" means the amount of the subject compound or combination that will elicit the biological or medical response of a tissue, system, animal or human that is being sought by the researcher, veterinarian, medical doctor or other clinician. For example, small molecule anti-cancer agent can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based anti-cancer agent, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

Radiation

The source of radiation of this invention can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the anti-cancer agent according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with other anti-cancer therapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention. In other words, the inhibition of tumor growth by means of the radiation treatment of the combination of this invention is enhanced when combined with treatment using an anti-cancer agent. Parameters of adjuvant radiation therapies are, for example, contained in International Patent Publication WO 99/60023. Further details of the methodology of radiation treatment of cancer patients is well known to those of skill in the art, and is readily available from the extensive literature in this area (e.g. Principles and Practice of Radiation Oncology (2003), 4th Edition, ISBN 0-7817-35254, ed. Perez C. A. et al., Lippincott Williams and Wilkins; Radiotherapy for head and Neck Cancers (2002), 2nd Edition, ISBN 0-7817-2650-6, Ang, K. K. and Garden, A. S., Lippincott Williams and Wilkins; Principles and Practice of Oncology (2001), 6th Edition, ISBN 0-7817-2387-6, ed. DeVita, V. T. et al., Lippincott Williams and Wilkins).

Additional Anti-Cancer Agents

In another aspect, the present invention provides a method for treating a cancer, comprising (a) identify a patient with acquired resistance to an EGFR kinase inhibitor; (b) administering to the patient an anti-cancer agent, and treating the patient with radiation therapy; and (c) administering one or more other cytotoxic, chemotherapuetic or anti-cancer agents, or compounds that enhance the effects of such agents.

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. Cytoxan®), chlorambucil (CHL; e.g. Leukeran®), cisplatin (CisP; e.g. Platinol®) busulfan (e.g. Myleran®), melphalan, carmustine (BCNU), streptozotcin, triethylenemelamine (TEM), mitomycin C, and the like; anti-metabolites, such as methotrexate (MTX), etoposide (VP16; e.g. Vepesid®), 6-mercaptopurine (6MP), 6-thioguanine (6TG), cytarabine (Ara-C), 5-fluorouracil (5-FU), capecitabine (e.g. Xeloda®), dacarbazine (DTIC), and the like; antibiotics, such as actinomycin D, doxorubicin (DXR; e.g. Adriamycin®), daunorubicin (daunomycin), bleomycin, mithramycin and the like; alkaloids, such as vinca alkaloids such as vincristine (VCR), vinblastine, and the like; and other antitumor agents, such as paclitaxel (e.g. Taxol®) and pactitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin, folinic acid, raltitrexed, and other folic acid derivatives, and similar, diverse antitumor agents. The following agents may also be used as additional agents: amifostine (e.g. Ethyol®), dactinomycin, mechlorethamine (nitrogen mustard), streptozocin, cyclophosphamide, lomustine (CCNU), doxorubicin lipo (e.g. Doxil®), gemcitabine (e.g. Gemzar®), daunorubicin lipo (e.g. Daunoxome®), procarbazine, mitomycin, docetaxel (e.g. Taxotere®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon alpha, interferon beta, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, and chlorambucil.

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering one or more anti-hormonal agents.

As used herein, the term "anti-hormonal agent" includes natural or synthetic organic or peptide compounds that act to regulate or inhibit hormone action on tumors.

Anti-hormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. Fareston®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as Zoladex® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g Antide®, Ares-Serono); the LHRH antagonist ganirelix acetate; the steroidal anti-androgens cyproterone acetate (CPA) and megestrol acetate, commercially available as Megace® (Bristol-Myers Oncology); the nonsteroidal anti-androgen flutamide (2-methyl-N-[4, 20-nitro-3-(trifluoromethyl)phenylpropanamide), commercially available as Eulexin® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834, 504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. Avastin™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. Vitaxin®); factors such as IFN-alpha (U.S. Pat. Nos. 4,1530,901, 4,503,035, and 5,231,176); angiostatin and plasminogen fragments (e.g. kringle 14, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists;

anti-angiogenesis agents such as MMP-2 (matrix-metalloprotienase 2) inhibitors and MMP-9 (matrix-metalloprotienase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004, 578, 606,046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering one or more tumor cell pro-apoptotic or apoptosis-stimulating agents.

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering one or more signal transduction inhibitors.

Signal transduction inhibitors include, for example: erbB2 receptor inhibitors, such as organic molecules, or antibodies that bind to the erbB2 receptor, for example, trastuzumab (e.g. Herceptin®); inhibitors of other protein tyrosine-kinases, e.g. imitinib (e.g. Gleevec®); ras inhibitors; raf inhibitors; MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer); GW-282974 (Glaxo Wellcome plc); monoclonal antibodies such as AR-209 (Aronex Pharmaceuticals Inc. of The Woodlands, Tex., USA) and 2B-1 (Chiron); and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering an anti-HER2 antibody or an immunotherapeutically active fragment thereof.

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering one or more anti-proliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217.

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering a COX II (cyclooxygenase II) inhibitor. Examples of useful COX-II inhibitors include alecoxib (e.g. Celebrex™), valdecoxib, and rofecoxib.

In yet another aspect, the present invention provides a method for treating a cancer, comprising (a) identify a patient with acquired resistance to an EGFR kinase inhibitor; (b) administering to the patient a therapeutically effective amount of an agent inhibiting EGFR kinase, and treating the patient with radiation therapy; and (c) administering one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

The following examples are presented to illustrate the present invention. They are not intended to limiting in any manner.

Example 1

Generation of In Vitro Erlotinib Resistant Model

Figure 1A:
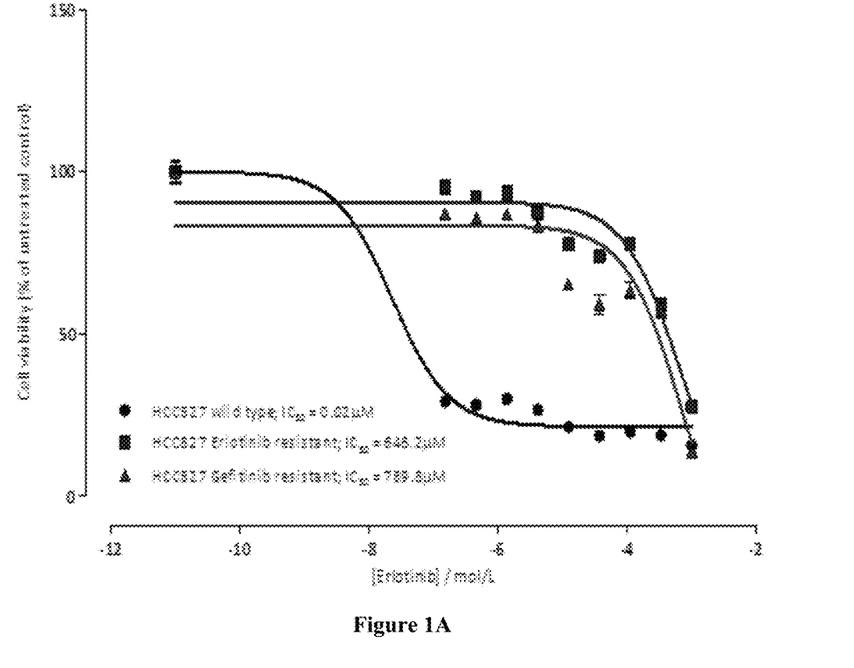
FIG. 1A. In vitro generation of resistance to Erlotinib using the HCC827 NSCLC adenocarcinoma cell line that harbors an activating EGFR mutation (del E746-A750). The Erlotinib resistant variant of HCC827 (ER1) was generated in vitro following sub-culture with escalating doses of Erlotinib. The resultant cell line exhibited a >1000 fold shift in $IC_{50}$ compared with the parental line.
Figure 1B:
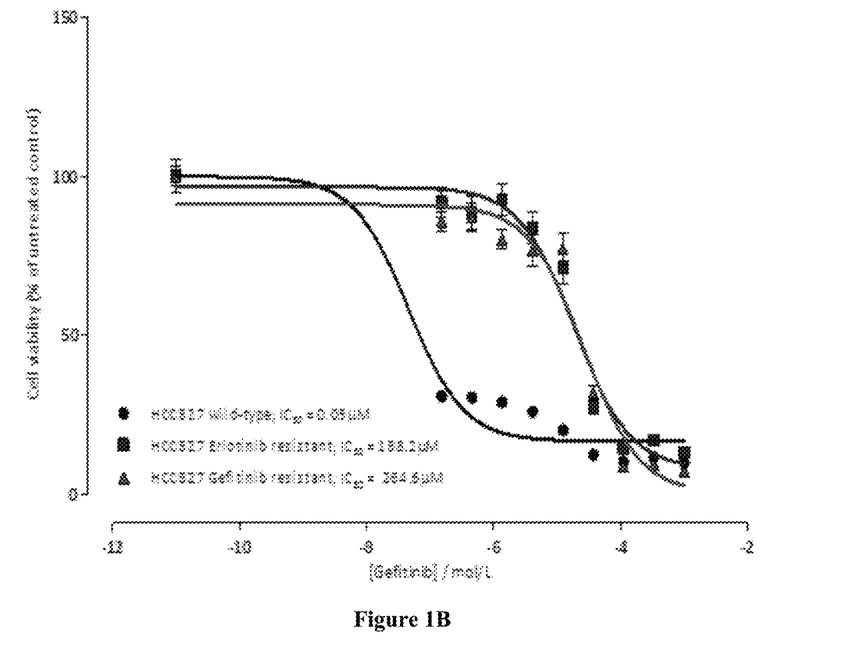
FIG. 1B. The Erlotinib resistant variant HCC827-ER1 exhibited cross-resistance with the alternate EGFR-TKI (Gefitinib).

HCC827 is an NSCLC adenocarcinoma cell line that harbors an activating EGFR mutation (del E746-A750). The Erlotinib resistant variant of HCC827 (ER1) was generated in vitro following sub-culture with escalating doses of Erlotinib. The resultant cell line exhibited a >1000 fold shift in $IC_{50}$ compared with the parental line (FIG. 1A) and exhibited cross-resistance with the alternate EGFR-TKI (Gefitinib) (FIG. 1B). Resistant material was characterized for further mutations in the EGFR gene by direct sequencing as well as for c-MET over expression and genomic amplification by quantitative PCR.

Figure 2A:
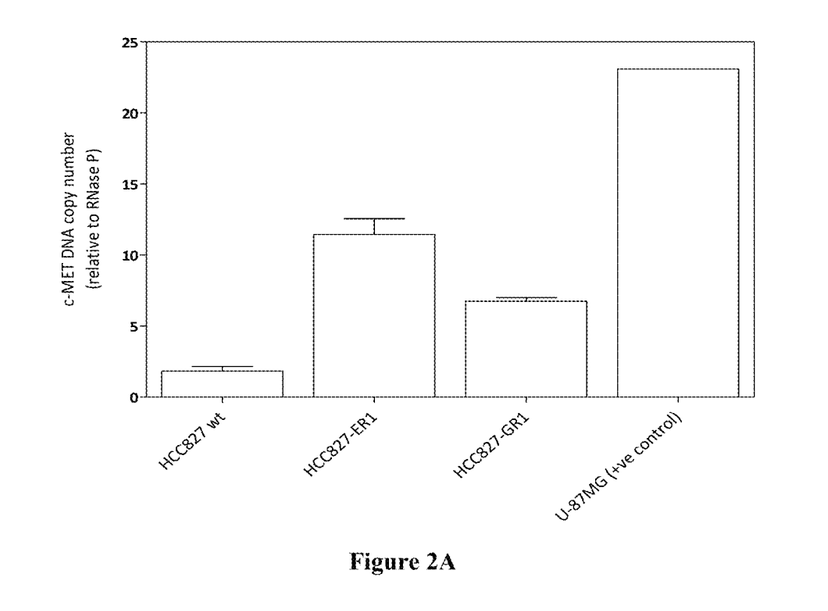
Figure 2B:
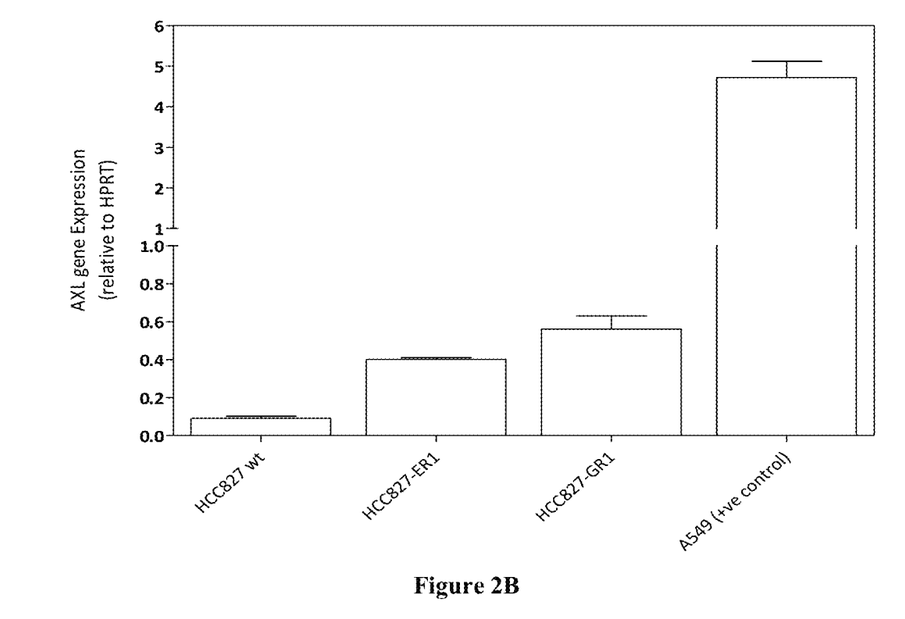
FIG. 2B. Erlotinib resistant variant of NSCLC cell line (HCC827-ER1) has increased AXL gene expression. Treatment naive and post-treatment resistance was characterized for mutations in EGFR by direct sequencing of exons 19 (del E746-A750) and 20 (T790M; gatekeeper). Exon 19 deletion was confirmed in all samples and no exon 20 T790M gatekeeper mutations were detected in any of the test samples. Samples were characterized for increased AXL gene expression via RT-PCR.

Treatment naive and post-treatment resistance was characterised for mutations in EGFR by direct sequencing of exons 19 (del E746-A750) and 20 (T790M; gatekeeper). Exon 19 deletion was confirmed in all samples and no exon 20 T790M gatekeeper mutations were detected in any of the test samples. Samples were also characterized for c-MET genomic amplification by qPCR and AXL gene expression via RT-PCR. HCC827-ER1 showed amplified c-MET copy number (FIG. 2A) and increased AXL gene expression (FIG. 2B).

Example 2

The effect of Erlotinib and Crizotinib alone and in combination with irradiation in A) HCC827 subcutaneous xenograft and B) HCC827-ER1 subcutaneous xenograft.

Methods

In Vitro Assay:

HCC-827 (NSCLC adenocarcinoma cell line with an activating EGFR mutation, del E746-A750) and HCC827-

ER (Erlotinib resistant variant) were grown in T25 flasks and treated with irradiation. Cells were counted after 6 days.

In Vivo Xenograft:

HCC-827 and HCC-827ER1 cells were implanted subcutaneously in nude mice (HsdOla:MF1-Foxn1$^{nu}$). Tumour measurements and body weights were taken 3 times weekly and treatment initiated when the tumours reached a mean volume of ~200 mm$^3$ (n=5 per group). Erlotinib was dosed at 25 mg/kg po QD.

In Vivo Irradiation:

Mice were anaesthetised and transported to the SARRP where CBCT (cone beam computed tomography) images were acquired. Using the MuriSlice software the isocenter of the tumour was identified and aligned with the central axis of the beam. Fractionated irradiation was administered with the SARRP (Small Animal Radiation Research Platform) (225 kV peak X-ray beams; dose rate of 2.5 Gy/min) using collimators of various diameters and a double beam (gantry position at 0° and 180°) under the guidance of the CBCT. A tolerability was performed initially to evaluate 3 Gy/day×5 days for 2 week.

Results

Figure 3:
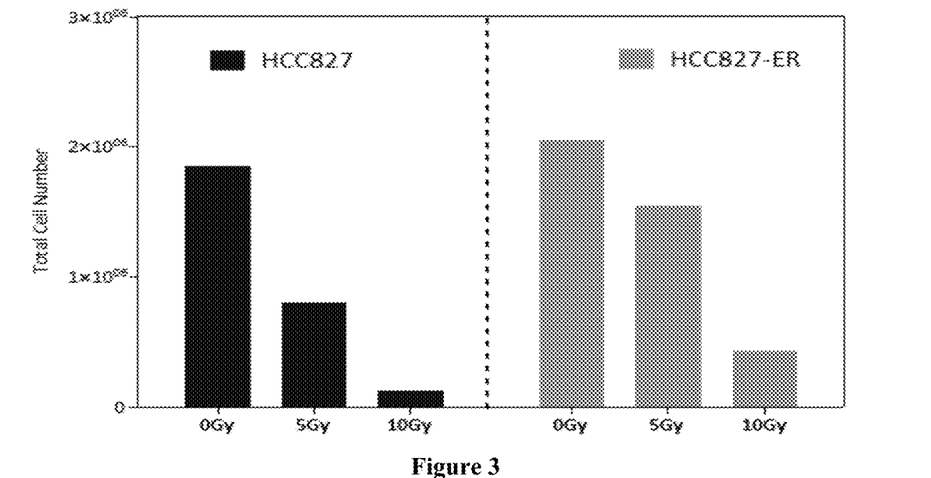
FIG. 3: Dose dependent effect of irradiation on cell number of HCC827 and HCC827-ER1 cells FIG. 4A. The effect of Erlotinib and Crizotinib alone and in combination with irradiation in HCC827 subcutaneous xenograft. Tumor volume is expressed as a percentage of the initial dose volume, and error bars represent SEM. When nude mice (HsdOla:MF1-Foxn1$^{nu}$) bearing s.c. HCC827 tumours (n=5/group) were dosed with Erlotinib alone or following irradiation the tumors regressed; however, there was no effect with Crizotinib alone.
Figure 4A:
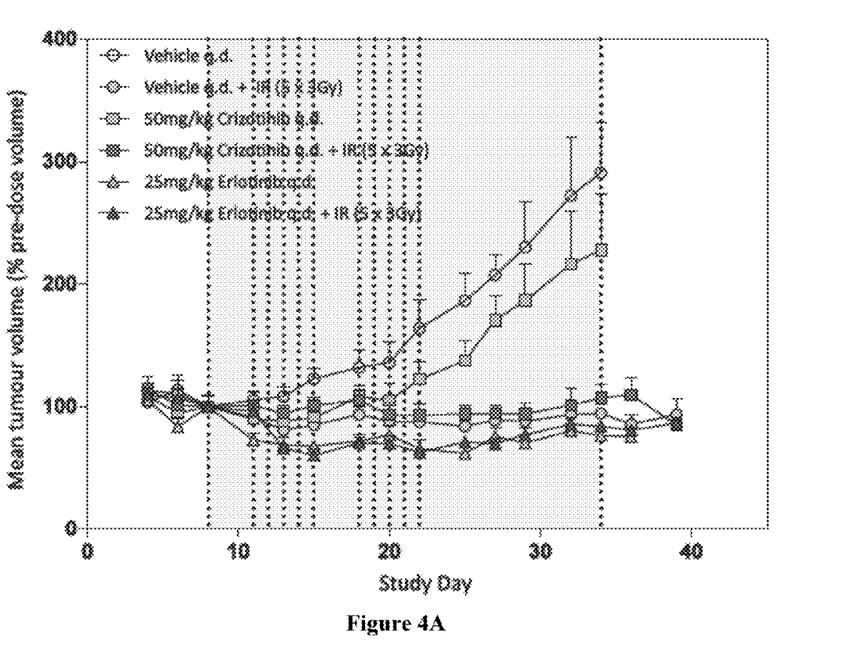
Figure 4B:
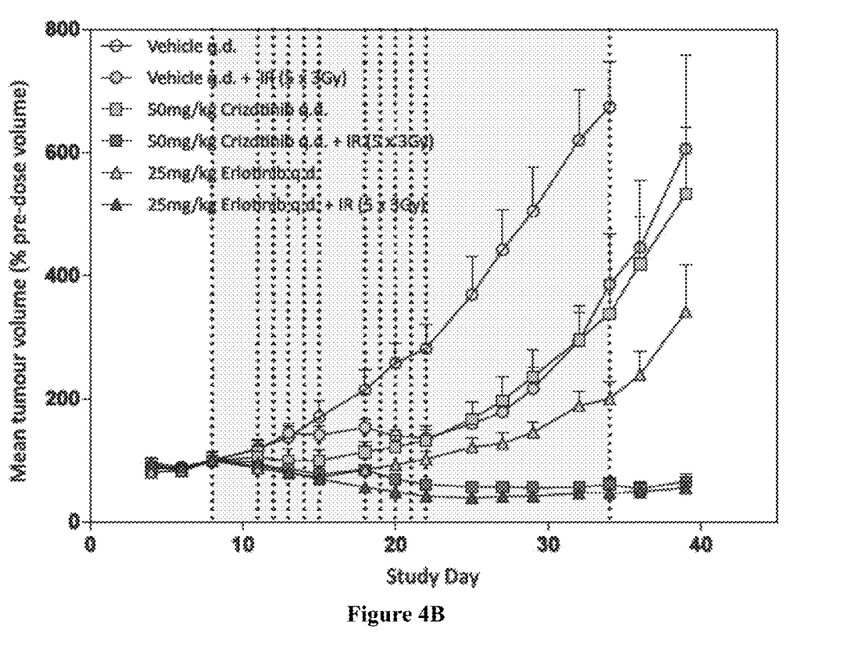

In Vitro Assay:

HCC-827 showed a dose-dependent killing effect in response to elevating levels of irradiation resulting in reduced cell number (FIG. 3). Similarly, the Erlotinib resistant line showed a dose response however the response to 5 Gy was markedly less than in the wild-type parental line suggesting that the acquired resistance to Erlotinib bestowed some resistance to irradiation In Vivo Assay:

Tumour volume is expressed as a percentage of the initial dose volume, error bars represent SEM. When nude mice (HsdOla:MF1-Fox1$^{nu}$) bearing s.c. HCC827 tumors (n=5/group) were dosed with Erlotinib alone or following irradiation the tumors regressed; however, there was no effect with Crizotinib alone (FIG. 4A). In comparison, when nude mice bearing s.c. HCC827-ER1 tumours (n=5/group, FIG. 4B) were dosed with Erlotinib or treated with irradiation, there was a significant reduction in tumour growth compared with vehicle (Two-way ANOVA, p<0.001; ~70% tumour growth inhibition) but no tumour regression. In clinical terms, this denotes progressive disease versus tumour regression and indicates treatment escape or emergence of resistance. When HCC827-ER1 tumors were dosed with Crizotinib there was a significant reduction in tumour growth compared with control (p<0.001; ~60% tumour growth inhibition), which confirmed the role of c-Met amplification in the resistance mechanism for HCC827-ER1. When Erlotinib or Crizotinib were combined with irradiation the tumour regression was restored demonstrated benefit of combination of Erlotinib or Crizotinib with irradiation in Erlotinib resistant setting where there is a c-MET gene amplification.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method for treating a patient having a lung cancer, comprising:
    (a) determining that the patient has acquired resistance to an EGFR kinase inhibitor;
    (b) detecting an amplification of c-MET gene copy in the patient; and
    (c) administering to the patient a therapeutically effective amount of Erlotinib with combination of radiation therapy.

2. The method of claim 1, wherein the EGFR kinase inhibitor is Erlotinib.

3. The method of claim 1, wherein the EGFR kinase inhibitor is Gefitinib.

4. The method of claim 1, wherein the lung cancer is NSCLC.

5. The method of claim 1, wherein the Erlotinib is administered to the patient by parenteral administration.

6. The method of claim 1, further comprising administering an agent selected from the group consisting of a chemotherapeutic agent, an anti-hormonal agent, an angiogenesis inhibitor, a pro-apoptotic agent and a signal transduction inhibitor.

7. A method for treating a patient having a lung cancer, comprising:
    (a) determining that the patient has acquired resistance to an EGFR kinase inhibitor;
    (b) detecting an amplification of c-MET gene copy in the patient; and
    (c) administering to the patient a therapeutically effective amount of Crizotinib with combination of radiation therapy.

8. The method of claim 7, wherein the EGFR kinase inhibitor is Erlotinib.

9. The method of claim 7, wherein the EGFR kinase inhibitor is Gefitinib.

10. The method of claim 7, wherein the lung cancer is NSCLC.

11. The method of claim 7, wherein the Crizotinib is administered to the patient by parenteral administration.

12. The method of claim 7, further comprising administering an agent selected from the group consisting of a chemotherapeutic agent, an anti-hormonal agent, an angiogenesis inhibitor, a pro-apoptotic agent and a signal transduction inhibitor.

* * * * *